(12) United States Patent
Williamson

(10) Patent No.: US 8,617,099 B2
(45) Date of Patent: Dec. 31, 2013

(54) INJECTION DEVICE PLUNGER AUTO-DISABLE

(75) Inventor: Daniel E. Williamson, Sherwood, OR (US)

(73) Assignee: Bioject Inc., Tigard, OR (US)

( * ) Notice: Subject to any disclaimer, the term of this patent is extended or adjusted under 35 U.S.C. 154(b) by 369 days.

(21) Appl. No.: 12/627,605

(22) Filed: Nov. 30, 2009

(65) Prior Publication Data

US 2010/0076374 A1 Mar. 25, 2010

Related U.S. Application Data

(63) Continuation-in-part of application No. 11/945,205, filed on Nov. 26, 2007, now abandoned.

(51) Int. Cl.
*A61M 5/30* (2006.01)
*A61M 5/00* (2006.01)

(52) U.S. Cl.
USPC .............................. 604/68; 604/110; 604/72

(58) Field of Classification Search
USPC ............................................. 604/68–72, 110
See application file for complete search history.

(56) References Cited

U.S. PATENT DOCUMENTS

| | | |
|---|---|---|
| 4,592,742 A | 6/1986 | Landau |
| 4,596,556 A | 6/1986 | Morrow et al. |
| 4,790,824 A | 12/1988 | Morrow et al. |
| 4,863,427 A | 9/1989 | Cocchi |
| 4,940,460 A | 7/1990 | Casey et al. |
| 4,941,880 A | 7/1990 | Burns |
| 4,946,441 A | 8/1990 | Laderoute |
| 5,062,830 A | 11/1991 | Dunlap |
| 5,064,413 A | 11/1991 | McKinnon et al. |
| 5,226,882 A | 7/1993 | Bates |
| 5,312,335 A | 5/1994 | McKinnon et al. |
| 5,312,577 A | 5/1994 | Peterson et al. |
| 5,383,851 A | 1/1995 | McKinnon, Jr. et al. |
| 5,399,163 A | 3/1995 | Peterson et al. |
| 5,503,627 A | 4/1996 | McKinnon et al. |
| 5,505,697 A | 4/1996 | McKinnon, Jr. et al. |

(Continued)

FOREIGN PATENT DOCUMENTS

| | | |
|---|---|---|
| CN | 1247475 A | 3/2000 |
| JP | 2001507963 A | 6/2001 |

(Continued)

OTHER PUBLICATIONS

Patent Cooperation Treaty, International Search Report for PCT Application No. PCT/US2008/084737, mailing date Jan. 27, 2009, 1 page.

(Continued)

*Primary Examiner* — Manuel Mendez
*Assistant Examiner* — Rebecca E Eisenberg
(74) *Attorney, Agent, or Firm* — Schwabe, Williamson & Wyatt, P.C.

(57) ABSTRACT

A nozzle assembly for a needle-free injection device. The nozzle assembly includes a nozzle body including an injectate chamber and one or more outlet orifices and a plunger configured to move through the injectate chamber toward the one or more outlet orifices. In some embodiments, the plunger includes a first portion and a second portion removably joined by a frangible region. In some embodiments, the plunger includes extensions configured to couple the plunger to a drive assembly of a needle-free injection device.

17 Claims, 7 Drawing Sheets

(56) References Cited

U.S. PATENT DOCUMENTS

| | | |
|---|---|---|
| 5,520,639 A | 5/1996 | Peterson et al. |
| 5,643,211 A | 7/1997 | Sadowski et al. |
| 5,746,714 A | 5/1998 | Salo et al. |
| 5,782,802 A | 7/1998 | Landau |
| 5,875,976 A * | 3/1999 | Nelson et al. .................. 239/600 |
| 5,893,397 A | 4/1999 | Peterson et al. |
| 5,921,967 A | 7/1999 | Sadowski et al. |
| 5,993,412 A | 11/1999 | Deily et al. |
| 6,096,002 A | 8/2000 | Landau |
| 6,132,395 A | 10/2000 | Landau et al. |
| 6,210,359 B1 | 4/2001 | Patel et al. |
| 6,216,493 B1 | 4/2001 | Weston et al. |
| 6,264,629 B1 | 7/2001 | Landau |
| 6,319,224 B1 | 11/2001 | Stout et al. |
| 6,383,168 B1 | 5/2002 | Landau et al. |
| 6,415,631 B1 | 7/2002 | Weston et al. |
| 6,471,669 B2 | 10/2002 | Landau |
| 6,506,177 B2 | 1/2003 | Landau |
| 6,572,581 B1 | 6/2003 | Landau |
| 6,585,685 B2 | 7/2003 | Staylor et al. |
| 6,607,510 B2 | 8/2003 | Landau |
| 6,623,446 B1 | 9/2003 | Navelier et al. |
| 6,641,554 B2 | 11/2003 | Landau |
| 6,645,170 B2 | 11/2003 | Landau |
| 6,648,850 B2 | 11/2003 | Landau |
| 6,676,630 B2 | 1/2004 | Landau et al. |
| 6,689,093 B2 | 2/2004 | Landau |
| 6,709,427 B1 | 3/2004 | Nash et al. |
| 6,716,190 B1 | 4/2004 | Glines et al. |
| 6,752,780 B2 | 6/2004 | Stout et al. |
| 6,752,781 B2 | 6/2004 | Landau et al. |
| 6,783,509 B1 | 8/2004 | Landau et al. |
| 6,935,384 B2 | 8/2005 | Landau et al. |
| 6,942,645 B2 | 9/2005 | Alexandre et al. |
| 6,979,310 B2 | 12/2005 | Navelier et al. |
| 6,981,961 B1 | 1/2006 | Navelier et al. |
| 7,056,300 B2 | 6/2006 | Alexandre et al. |
| 7,156,823 B2 | 1/2007 | Landau et al. |
| 2002/0151839 A1 | 10/2002 | Landau |
| 2004/0111054 A1 | 6/2004 | Landau et al. |
| 2005/0119608 A1 | 6/2005 | Landau et al. |
| 2005/0154347 A1 | 7/2005 | Neracher |
| 2005/0165349 A1 | 7/2005 | Stamp |
| 2005/0209553 A1 | 9/2005 | Landau |
| 2006/0178625 A1 * | 8/2006 | Lim et al. ...................... 604/110 |
| 2006/0189927 A1 | 8/2006 | Alexandre et al. |

FOREIGN PATENT DOCUMENTS

| | | |
|---|---|---|
| JP | 2005532126 A | 10/2005 |
| WO | WO 98/28030 A1 | 7/1998 |
| WO | 0072908 | 12/2000 |

OTHER PUBLICATIONS

Patent Cooperation Treaty, Written Opinion of the International Searching Authority for PCT Application No. PCT/US2008/084737, mailing date Jan. 27, 2009, 4 pages.

Notice of Reason for Rejection mailed Jan. 29, 2013 for Japanese Application No. 2010-535115, 5 pages.

* cited by examiner

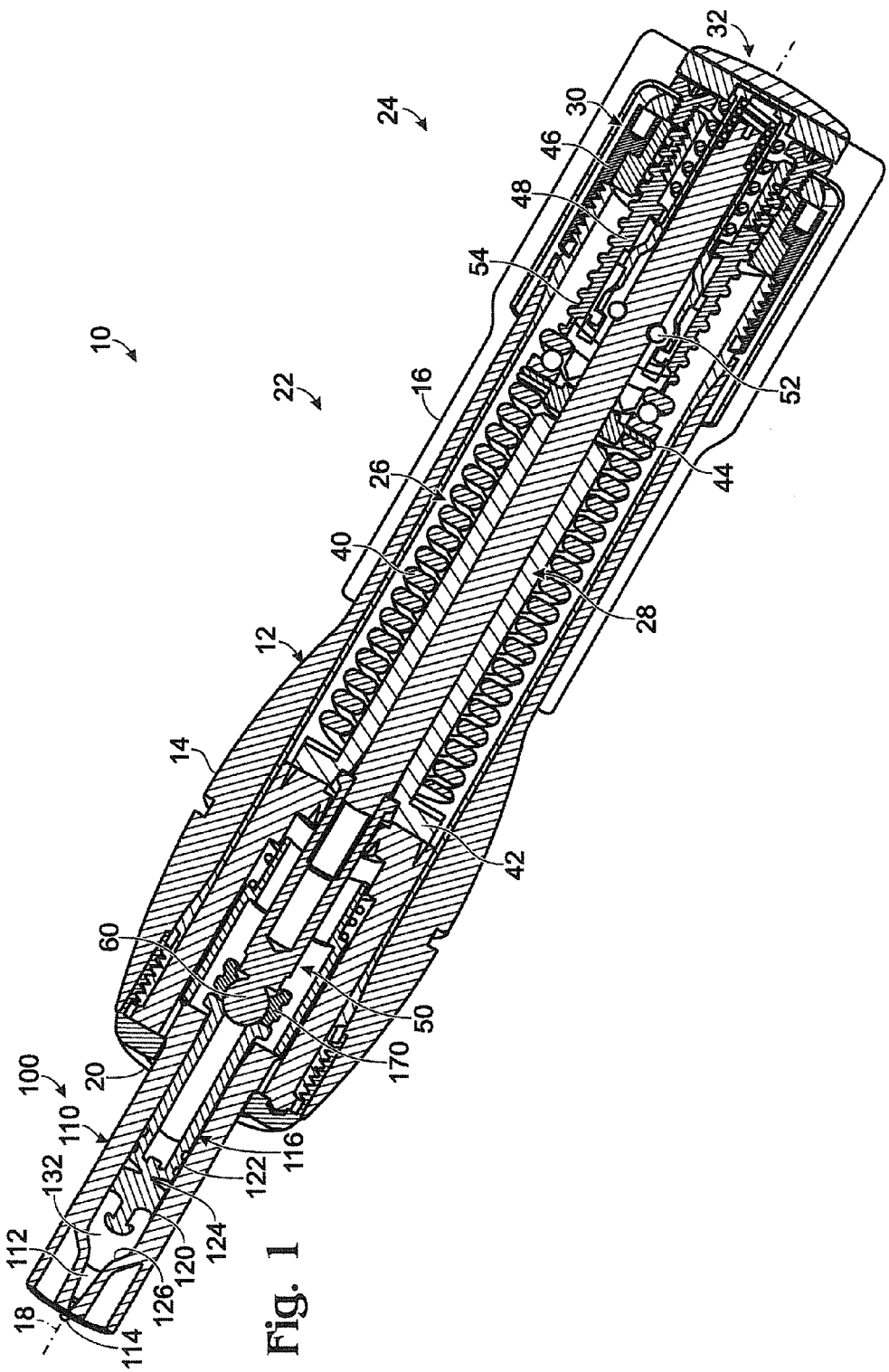

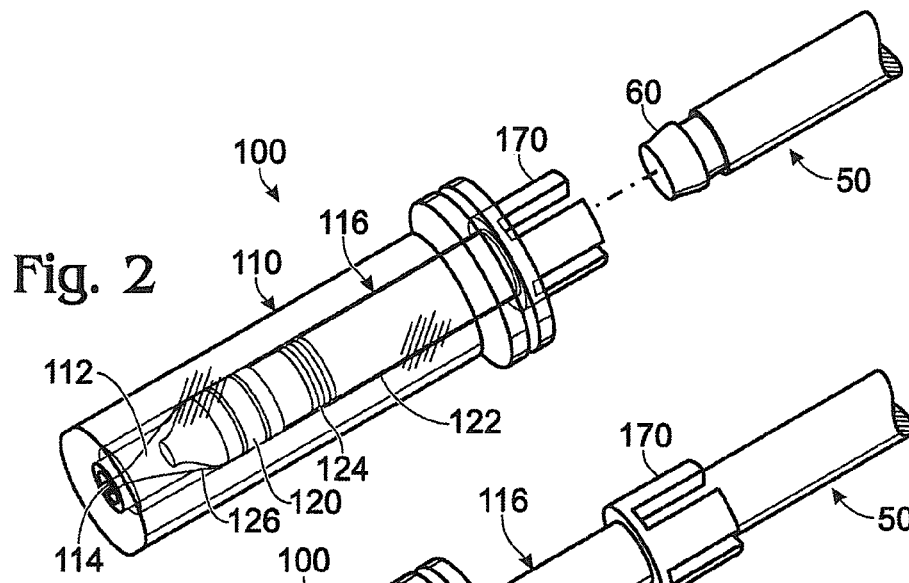
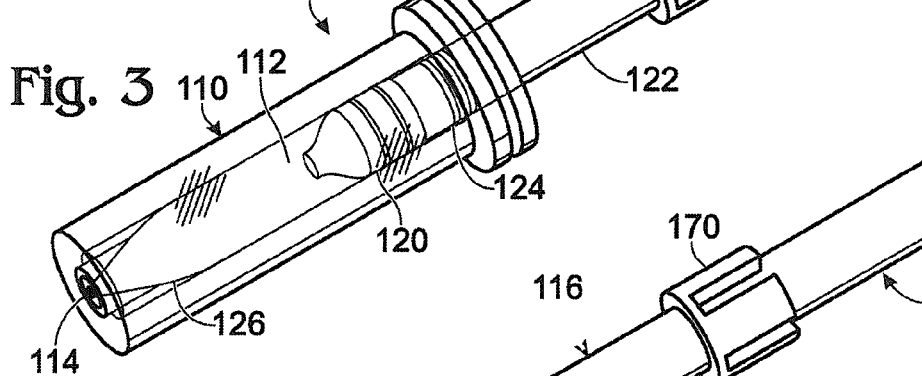
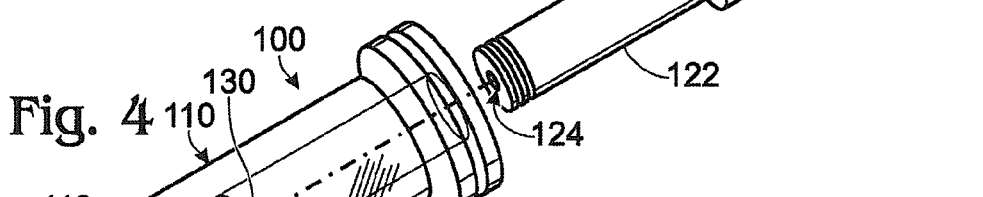
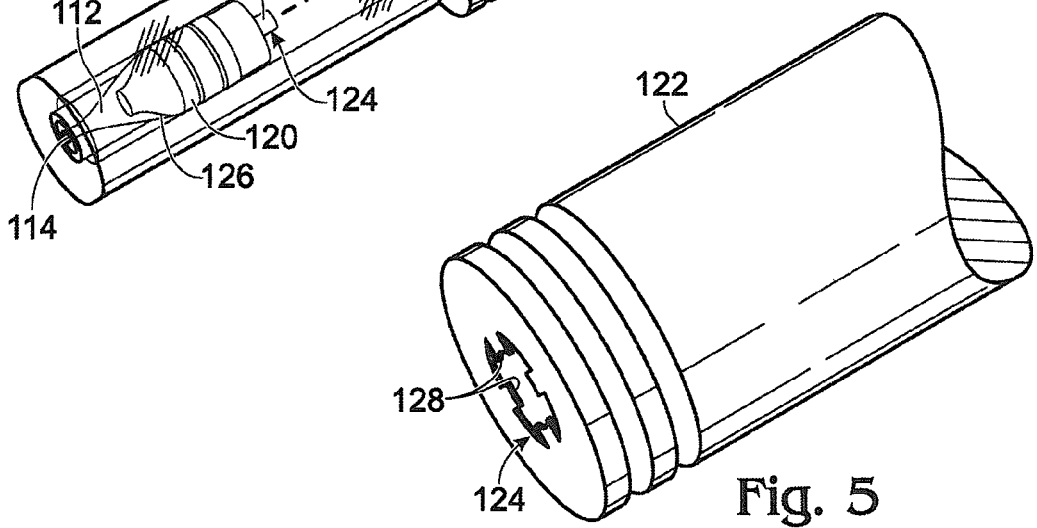

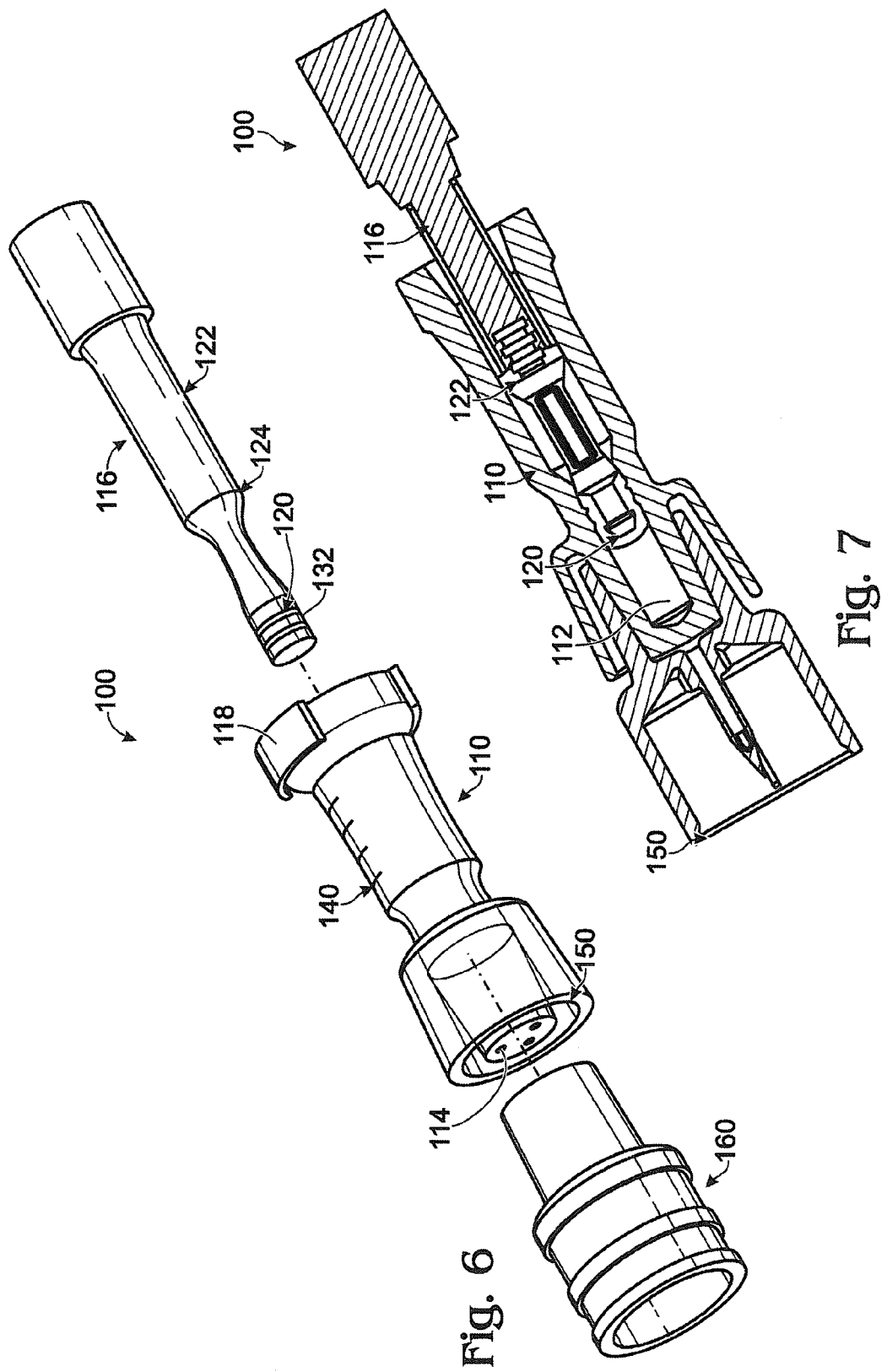

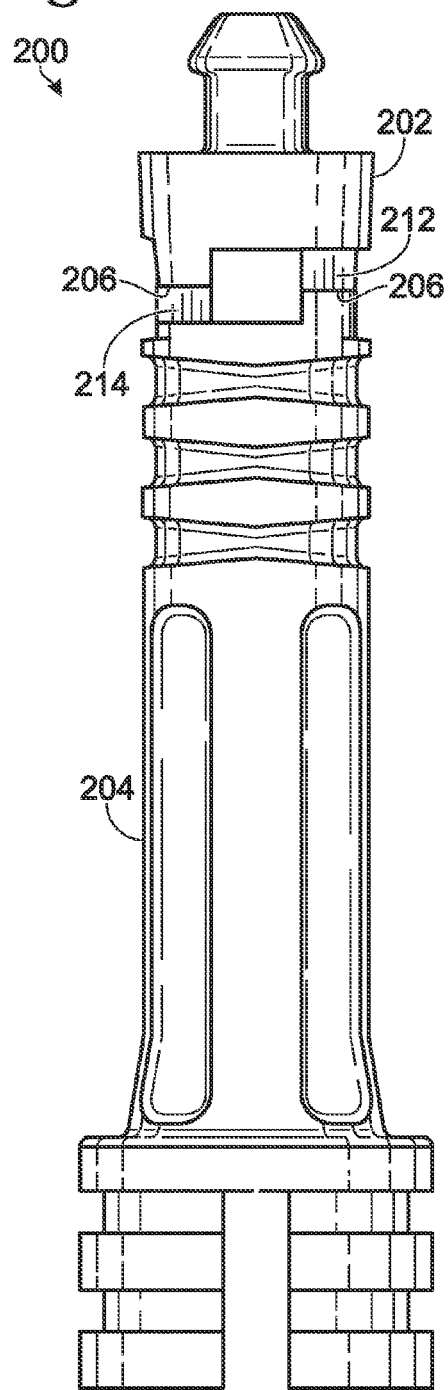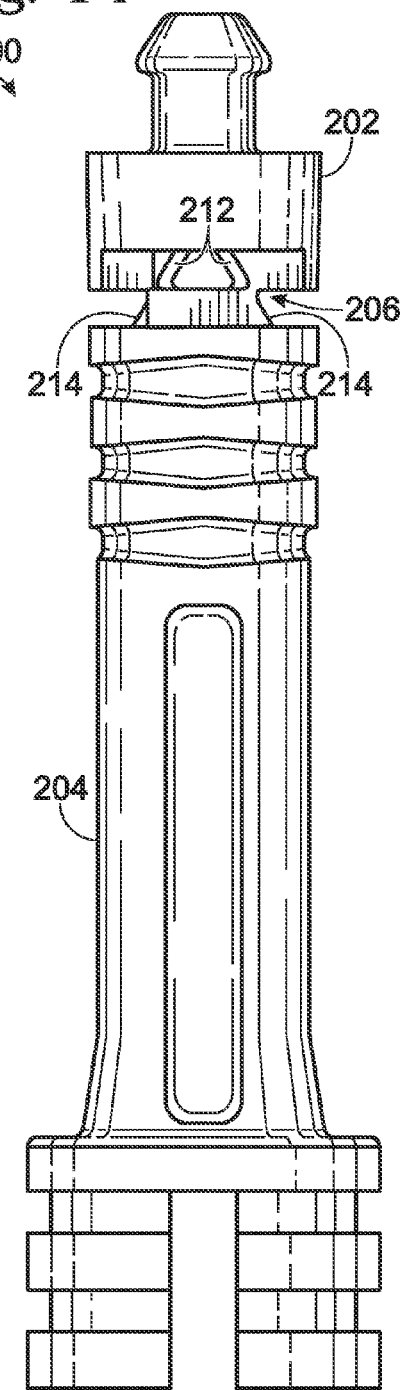

INJECTION DEVICE PLUNGER AUTO-DISABLE

CROSS-REFERENCE TO RELATED APPLICATIONS

This application is a continuation-in-part of U.S. patent application Ser. No. 11/945,205 entitled "NEEDLE-FREE INJECTION DEVICE WITH NOZZLE AUTO-DISABLE," and is related to U.S. patent application Ser. No. 11/945,212, entitled "NEEDLE-FREE INJECTION DEVICE WITH AUTO-DISABLE," both which were filed Nov. 26, 2007. The disclosures of each application are incorporated herein by reference.

BACKGROUND

Needle-free injection systems provide an alternative to standard fluid delivery systems, which generally use a needle adapted to penetrate the outer surface of a target. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

Examples of needle-free injection systems and components are found in U.S. Pat. Nos. 4,592,742, 4,596,556, 4,790,824, 4,940,460, 4,941,880, 5,062,830, 5,064,413, 5,312,335, 5,312,577, 5,383,851, 5,399,163, 5,503,627, 5,505,697, 5,520,639, 5,746,714, 5,782,802, 5,893,397, 5,993,412, 6,096,002, 6,132,395, 6,216,493, 6,264,629, 6,319,224, 6,383,168, 6,415,631, 6,471,669, 6,506,177, 6,572,581, 6,585,685, 6,607,510, 6,641,554, 6,645,170, 6,648,850, 6,623,446, 6,676,630, 6,689,093 6,709,427, 6,716,190, 6,752,780, 6,752,781, 6,783,509, 6,935,384, 6,942,645, 6,979,310, 6,981,961, 7,056,300 and 7,156,823; U.S. Patent Application Publication Nos. 2005/0119608 and 2006/0189927; and International Publication No. WO 00/72908, the disclosures of which are incorporated herein by reference, in their entirety and for all purposes.

SUMMARY

The present disclosure is directed to auto-disable plungers and nozzle assemblies including such plungers for use in both traditional and needle-free injection devices. The disclosed nozzle assembly includes a nozzle body including an injectate chamber and one or more outlet orifices and a plunger configured to move through the injectate chamber toward the one or more outlet orifices. In some embodiments, the plunger includes a first portion and a second portion removably joined by a frangible region. In some embodiments, the plunger includes deformable extensions configured to selectively couple the plunger to a drive assembly of a needle-free injection device.

The advantages of the disclosed nozzle assembly may be understood more readily after a consideration of the drawings and the Detailed Description.

BRIEF DESCRIPTION OF THE DRAWINGS

FIG. 1 is a cross-sectional view of an example of a nozzle assembly coupled with an example of a needle-free injection device having a delivery system and an actuation system.

FIG. 2 illustrates a nozzle assembly being coupled to a delivery system of a needle-free injection device, the nozzle assembly includes a nozzle body and a plunger.

FIG. 3 illustrates the nozzle assembly of FIG. 2 being retracted by the delivery system to draw a dose of injectate into the nozzle assembly.

FIG. 4 illustrates the nozzle assembly of FIG. 3 after delivery of an injection in which the plunger breaks along a frangible region such that a portion of the plunger remains in the nozzle body.

FIG. 5 illustrates an example of a frangible region for a plunger.

FIG. 6 illustrates an example of a nozzle assembly including an intradermal nozzle assembly and a vial adapter.

FIG. 7 illustrates a cross-sectional view of an intradermal nozzle assembly.

FIG. 13 illustrates another embodiment of a plunger that includes a distal portion and a proximal portion that are configured to uncouple along a frangible region upon injection.

FIG. 14 depicts the plunger of FIG. 13 rotated approximately 90 degrees.

DETAILED DESCRIPTION

Figure 8:
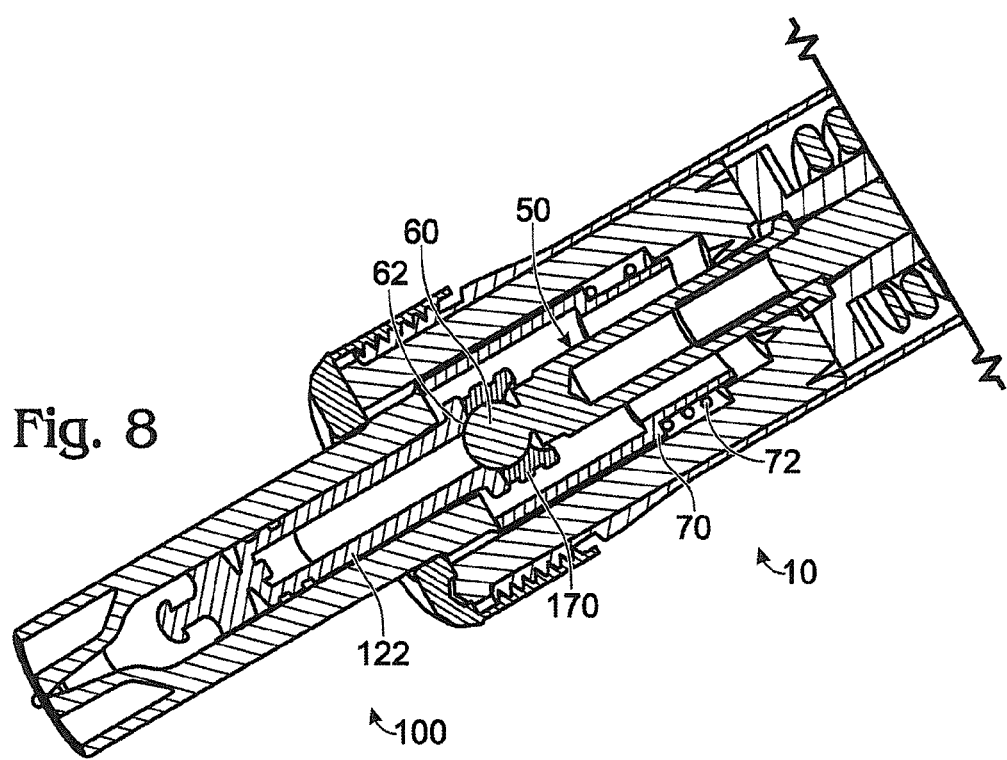
FIG. 8 illustrates a nozzle assembly including a plunger having extensions to couple the plunger to a ram of a delivery system; the ram includes a curved portion.
Figure 9:
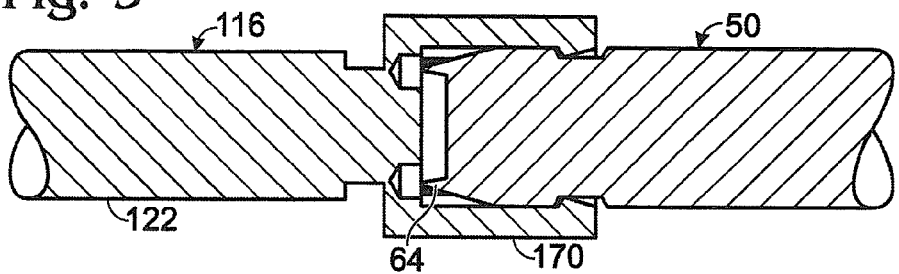
FIG. 9 illustrates a nozzle assembly including a plunger having extensions to couple the plunger to a ram of a delivery system; the ram includes a cutting portion.

FIG. 1 illustrates an example of a needle-free injection device 10 and a nozzle assembly 100. Although the disclosed injection device is intended to be reusable, the nozzle assembly includes various auto-disable features to restrict reuse of the nozzle assembly. The nozzle may be replaced, for example, after every injection or after a set number of injections.

Device 10 includes a body 12 to enclose various systems used to effect an injection. The body is typically sized and shaped to be comfortably held in a user's hand and may take any suitable configuration. Body 12 may be formed from injection-molded plastic, though various other materials and fabrication methods may be suitable.

As illustrated in FIG. 1, body 12 may be comprised of various subsections, such as housings 14, 16. The housings may be configured to move relative to one another to actuate the various systems. In the example shown in FIG. 1, one or more of the housings may be rotatable relative to another housing and/or rotatable about a central axis 18 to actuate various assemblies of the device.

The body includes an opening 20 in an end of the device to receive the nozzle assembly. The body may include other apertures, such as one or more view ports, to provide feedback or instructions to a user of the device. The apertures may align with indicia, such as arrows or text, which instruct a user in proper operation of the device or convey information to a user, such as the current configuration or status of the device.

Nozzle assembly 100 is configured to be selectively coupled to the delivery system. The nozzle assembly houses an injectate and provides an interface with a recipient's skin. As illustrated in FIGS. 1-4, nozzle assembly 100 includes a nozzle body 110 forming an injectate chamber 112 with one or more outlet orifices 114. The nozzle assembly further includes a plunger 116 configured to move through the injectate chamber toward the orifice to expel an injectate.

Device 10 may include one or more systems to effect an injection. For example, the device of FIG. 1 includes a delivery system 22 and an actuation system 24. Delivery system 22 provides an interface for delivery of an injectate to a recipient and delivers an injection by expelling the injectate from the device. Delivery system 22 is configured to expel a volume of fluid from the device, such as a drug. The word "drug" as used herein is intended to encompass, for example, and without limitation, any medication, pharmaceutical, therapeutic, vaccine, aesthetic or other material which can be administered by injection. Actuation system 24 prepares the device for delivery of an injection and actuates delivery of an injection.

Delivery system 22 includes a drive assembly 26 to provide a driving force to effect an injection. In some versions of the device, a transmission assembly 28 may be provided to couple the nozzle assembly and the drive assembly.

Actuation system 24 includes a preparation assembly 30, such as a winder, to selectively arrange the drive assembly to provide a drive force to deliver an injection. A trigger assembly 32 assists a user in selectively actuating the drive assembly, directly or indirectly via the transmission assembly, to deliver an injection.

The structure and operation of needle-free injection devices configured to receive nozzle assembly 100 may include those disclosed in U.S. Published Patent Application No. 2005/0119608 and related U.S. patent application entitled "NEEDLE-FREE INJECTION DEVICE WITH AUTO-DISABLE," filed Nov. 26, 2007. In the illustrative device shown in FIG. 1, drive assembly 26 includes a drive source 40, such as a spring, disposed between spring stop members 42, 44 such that bringing the spring stop members closer together compresses the spring, while decompression of the spring pushes the stop members away from one another. Relative rotation between housing sections, such as rotation of housing 16 relative to housing 14, actuates winder 30, which urges the distal spring stop towards the proximal spring stop to compress the spring. When the spring is compressed, the device is referred to as being in a wound configuration. In the example of FIG. 1, winder 30 may be rotated in a first direction and act on an internal winding nut 46 to translate a screw 48 relative to the winding nut, thereby moving the distal spring stop to the left.

As also shown in FIG. 1, nozzle assembly 100 may be coupled to the device by placing the nozzle assembly through opening 20 in the device, such as by inserting the nozzle assembly along axis 18. The nozzle body may include one or more guides 118, as shown in FIGS. 2-4 and 6, to assist a user in locating the nozzle assembly relative to the device. The guide and opening may be similarly shaped to assist a user in aligning the nozzle assembly. For example, as shown in FIG. 6 the nozzle body may be configured to be inserted into the device and then rotated to lock the guides into the device.

In the example shown in FIG. 1, insertion of the nozzle assembly alters the configuration of the device so that an injection may be performed. Consequently, the device is disabled (i.e., prevented from releasing the spring) until a nozzle assembly is engaged. For example, the nozzle assembly of FIG. 1 moves the transmission assembly 28, such as in the form of a ram 50 that extends along the central axis of the device, to the right which allows one or more locking members 52 to engage the ram, thereby coupling the actuation system to the delivery system. Since rearward movement of the ram engages the proximal spring stop, the spring stop members are then coupled to one another and ready to be retracted relative to housing 14 to withdraw the ram and plunger, thereby drawing a dose into the nozzle body.

The rear housing 16 may be rotated in a second direction (opposite the first direction during spring compression) to withdraw the plunger and both spring stop members (to the right with respect to FIG. 1). Movement of the plunger to the right, as shown in FIG. 1, draws an injectate into chamber 112 through orifice(s) 114. During dosing, housings 14 and 16 may translate relative to one another as needed.

To deliver an injection, the trigger assembly 32, such as in the form of a button, is actuated to urge the ram and plunger towards the outlet orifice(s). For example, as the trigger assembly in FIG. 1 is pressed, a bushing 54 is urged towards the outlet orifices and provides a recess to receive locking members 52. The ram is therefore free to travel through the device. Since the distal spring stop is still held in place, decompression of the spring urges the proximal spring stop member towards the outlet orifice(s), which moves the ram and plunger towards the orifice(s) to deliver an injection.

In the example shown in FIGS. 1-4, nozzle plunger 116 includes first and second portions 120, 122 coupled together by a frangible region 124. The first portion 120 may be referred to as the proximal portion since it is closest to the outlet orifice. The second portion 122 may be referred to as the distal portion or base since it is further from the outlet orifice. The proximal portion may be configured to uncouple from the distal portion along the frangible region and lodge in a proximal end of the injectate chamber, thereby preventing intake of an injectate into the nozzle body. For example, to restrict reuse of the nozzle assembly, the proximal portion may remain in the injectate chamber, such as in a lead-in section 126 adjacent the orifice, upon retraction of the distal portion of the plunger from the injectate chamber.

The frangible region may be configured to yield in response to a force applied along a longitudinal axis of the plunger (along central axis 18, as shown in FIG. 1). For example, ram 50 may include an impact region 60 to apply a suitable force to the frangible region upon triggering of an injection. As shown in FIG. 1, as ram 50 moves toward outlet orifice(s) 114 and completes delivery of an injection. The continued force of impact region 60 against the plunger may urge distal portion 122 of the plunger forwards. However, since proximal portion 120 is prevented from moving further by the interior of the nozzle body, such as lead-in section 126, the frangible region breaks, as illustrated in FIG. 4. The proximal portion may become lodged in the nozzle body to prevent reuse of the nozzle assembly. Further, since there is no contact between the injectate and the distal portion, the distal portion may be removed from the ram without requiring a user to have contact with the injectate.

FIGS. 4 and 5 illustrate an example of a frangible region 124 after the proximal portion has been separated from the distal portion of the plunger. As shown, the frangible region includes fingers 128 that may be broken away, such as from a post 130, to separate the plunger portions.

As shown in FIGS. 1-4 and 6, the plunger may be at least partially visible through the nozzle body. The plunger may include first and second visibly distinct regions such that movement of the plunger through the nozzle body is measurable. For example, proximal portion 120 may include an over-molded tip 132, as best seen in FIG. 1, so that the tip is visibly distinct from the rest of the proximal portion. In other configurations, the proximal portion may be visibly distinct from the distal portion. Injectate chamber 112 may include a dose scale 140, as shown in FIG. 6, to incrementally measure the volume of the injectate drawn into the chamber. In some versions of the device, the dose scale includes indicia and the first and second visibly distinct regions of the plunger are configured to align with the indicia. Additionally or alternatively, the dose scale may be a pre-molded dose scale having ribs to indicate each unit of measure.

FIG. 6 further illustrates a nozzle assembly 100 suitable for delivering intradermal injections. The intradermal nozzle assembly may include several outlet orifices 114. For example, the nozzle assembly may include three orifices arranged in a triangular configuration, four orifices arranged in a square configuration, and the like. The outlet orifices may be laser drilled to produce orifice diameters that are smaller than those provided on typical nozzle assemblies. For example, the outlet orifices may have diameters equal to or smaller than 0.003 inch. The outlet orifices may be formed using the methods described in U.S. patent application Ser. No. 11/765,245, the disclosure of which is incorporated herein by reference.

As shown in FIGS. 6 and 7, plunger 116 includes a proximal portion 120 and a distal portion 122 having different diameters. For example, the distal portion may have a diameter that is larger than the diameter of the proximal portion. The reduced diameter portion acts as a pressure multiplier and allows for greater dose accuracy, such as for intradermal doses between 50 and 150 μL. For example, decreasing the plunger diameter while maintaining the spring force increases the pressure used to deliver an injection without changing the travel length of the ram and plunger. A multiple orifice nozzle in combination with a reduced plunger diameter therefore provides an increased delivery pressure from the same device. For example, the device disclosed in FIG. 1 may be coupled with nozzle assemblies having distal plunger portions with diameters suitable for coupling with transmission assembly 28, yet having proximal plunger portions with diameters suitable for delivering injections at different tissue depths. The device and corresponding spring 40 and spring travel length may be used with nozzle assemblies having proximal plunger diameters suitable for delivering intradermal, subcutaneous, and intramuscular injections. The reduced plunger diameter may enable use of a greater range of materials from which plunger 116 may be formed. For example, the plunger may provide first and second visibly distinct regions, as previously described, by using different plunger materials so that movement of the plunger through the nozzle body is more easily measurable, thereby providing greater dose accuracy. The two diameter plunger may be formed of different materials so that each diameter is formed of a plastic resin of different colors. For example, the plunger may be formed in an injection molding machine as a single piece using the process of "overmolding" or "two-shot molding" so that a portion of the plunger is a different color than the rest of the plunger.

The nozzle assembly may include a tension ring 150 for maintaining skin tension of a recipient during an injection. A vial adapter 160 may engage the nozzle body to couple the nozzle assembly to a vial of injectate during dosing of the nozzle assembly. The vial adapter may be coupled to a multiple orifice nozzle using a luer taper engagement.

Another way of preventing nozzle assembly reuse is by providing a nozzle assembly having an auto-disable that prevents the plunger and ram from being coupled together after an injection is performed. For example, a portion of the plunger may be deformable to restrict coupling of the plunger with the ram after delivery of an injection. In the following examples, the nozzle assembly is coupled to the device so that the plunger couples to the drive assembly, such as by snapping onto the ram. The device may then be wound, armed, and dosed as previously described to prepare for an injection. Once the device has been actuated, the ram may deform a portion of the nozzle assembly, such as a portion of the plunger, to prevent reuse of the nozzle assembly. The ram may be formed from a hard and/or substantially rigid material, such as steel, whereas the plunger may be formed from a brittle, soft and/or substantially deformable material, such as plastic, particularly high impact polysterene or polycarbonate.

FIGS. 8-12 illustrate deformable plungers to restrict reuse of a nozzle assembly. Distal portion 120 of plunger 116 may include extensions 170 configured to couple the plunger to a drive assembly of a needle-free injection device. To restrict reuse of the nozzle assembly, the extensions may be configured to deform upon firing of the device, such as in response to a force applied along a longitudinal axis of the plunger. In the example shown in FIG. 8, ram 50 includes impact region 60 which is configured to apply a force to the plunger to deliver an injection and deform a set of extensions radially outward so that the plunger is unable to grip the ram. The ram is therefore unable to retract the plunger to draw a second dose into the nozzle assembly.

Figure 10:
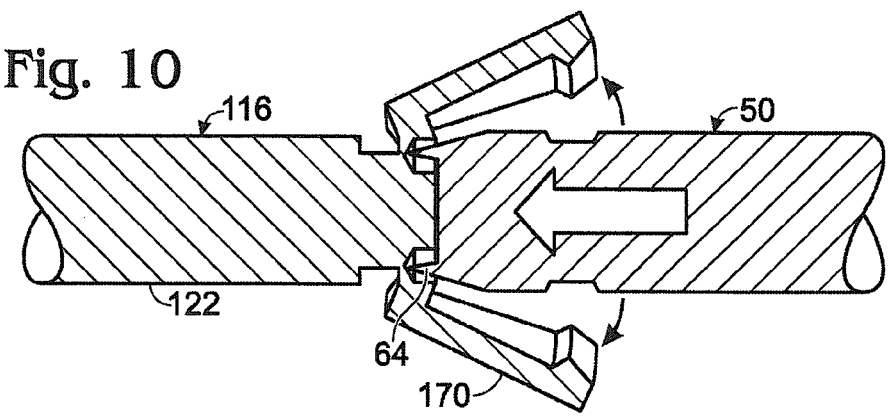
FIG. 10 illustrates the nozzle assembly of FIG. 9 with the extensions deformed away from the ram.
Figure 11:
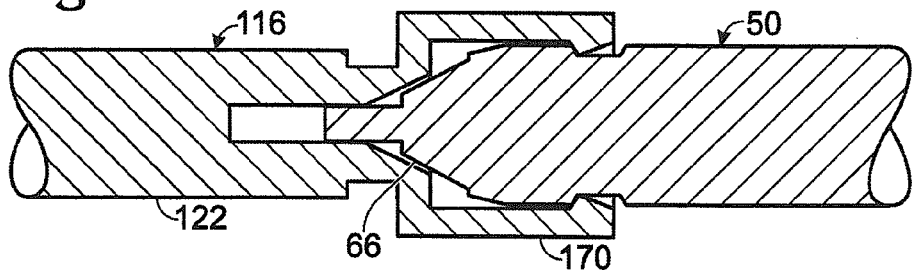
FIG. 11 illustrates a nozzle assembly including a plunger having extensions to couple the plunger to a ram of the delivery system; the ram includes an angled portion.

The extensions may be configured to couple the plunger to various geometries, such as to variously shaped ram impact regions 60. The impact region may include a curved portion 62 configured to urge the extensions away from the transmission member. For example, as shown in FIG. 8, the distal portion 122 of the plunger may include extensions configured to grip a spherical impact region of the ram that deforms the extensions outward to prevent the extensions from further gripping the ram. In the example shown in FIGS. 9 and 10, the impact region of the ram may include a sharp region, such as a cutting portion 64 that is configured to deform a set of extensions outward upon impact (as shown in FIG. 10). The ram may therefore deform a portion of the plunger through circumferential shear at the beginning of device actuation. In some configurations of the device, the ram may include an angled portion 66, such as a wedge-shaped impact region, that urges a set of extensions apart so that the ram is no longer gripped by the extensions once the device has been fired. The wedge may also be in the form of a separate member that is driven into the aft end (i.e., the distal portion) of the plunger to drive the extensions apart. This component may remain in the plunger to prevent the extensions from being forced back into place in an attempt to bypass the auto-disable mechanism.

Figure 12:
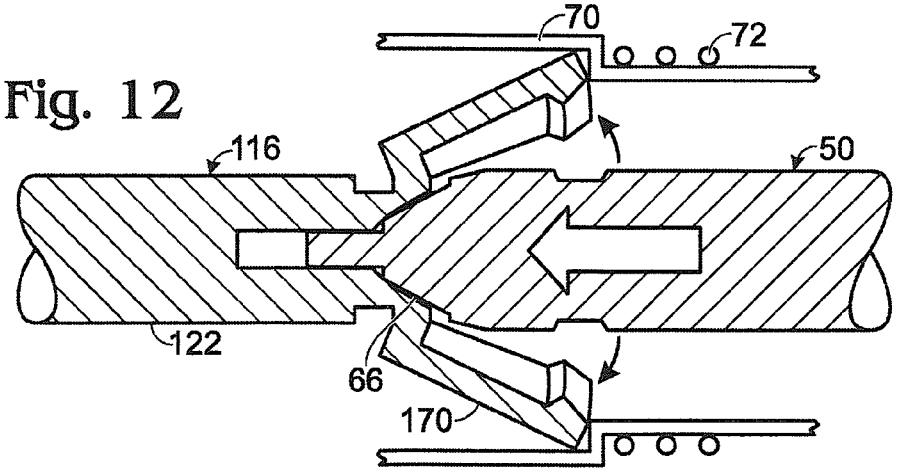
FIG. 12 illustrates the nozzle assembly of FIG. 11 with the extensions deformed away from the ram.

As shown in FIGS. 1 and 8, the needle-free injection device may include a release mechanism 70, such as a ramp, to receive the deformed extensions. The ramp may be biased, such as by spring 72, to urge the plunger away from the ram, and thereby assist in removing the used nozzle assembly. For example, as illustrated in FIG. 12, once the extensions 170 are deformed outward, the extensions catch on ramp 70. Retraction of the ram would then merely pull the ram out of engagement with the plunger.

FIGS. 13-16 depict another embodiment of a plunger 200 including a proximal portion 202 and a distal portion 204 that are configured to uncouple along a frangible region 206 upon injection. FIGS. 13 and 14 depict plunger 200 at two different angles. Plunger 200 may be configured to move through an injectate chamber (e.g., 112 described above) of a needle-free device toward an outlet orifice (e.g., 114 described above). These components may be configured specifically to increase the likelihood that proximal portion 202 remains in the injectate chamber upon retraction of distal portion 204 from the injectate chamber.

Figure 15:
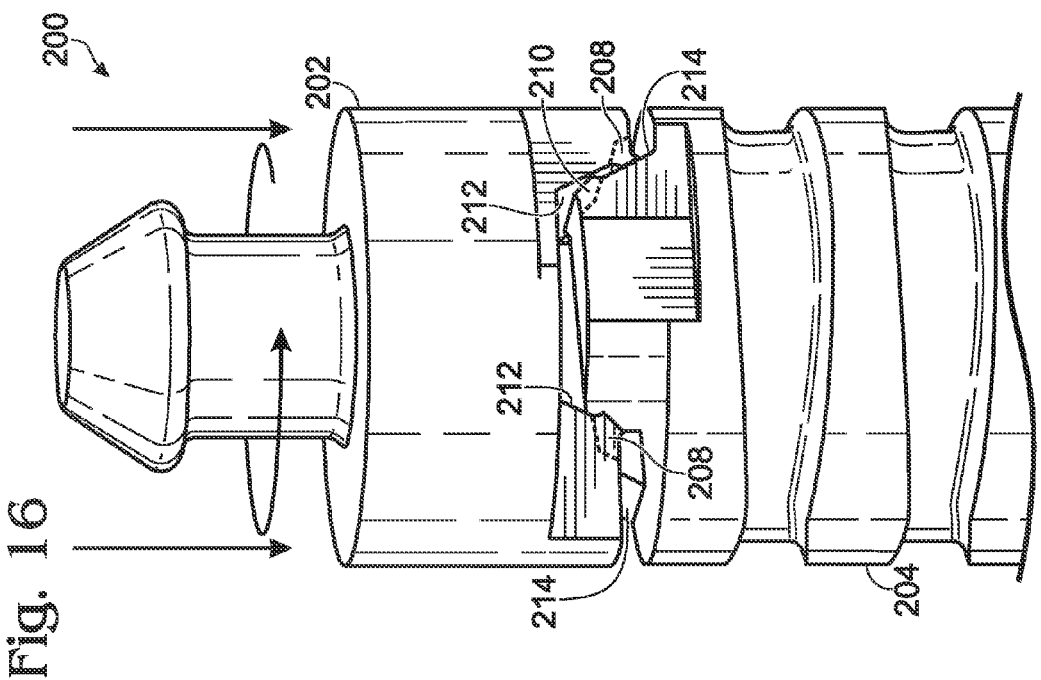
FIG. 15 depicts the plunger of FIGS. 13-14 from a closeup perspective.
Figure 16:
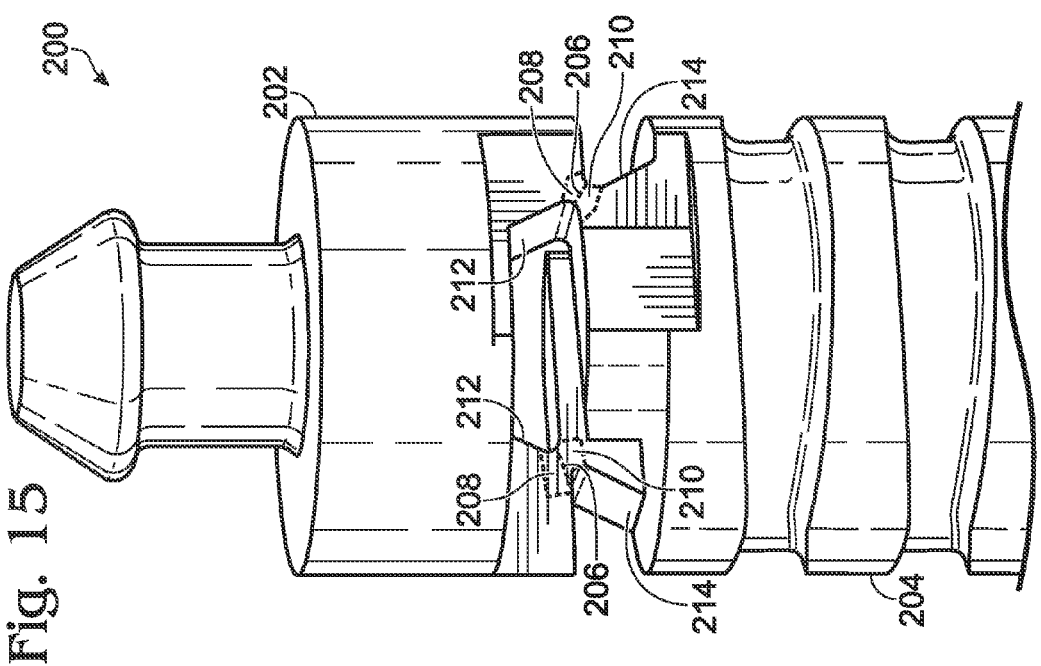
FIG. 16 depicts the plunger of FIGS. 13-15 after the proximal and distal portions have uncoupled along the frangible region.

Referring now to FIGS. 15 and 16, frangible region 206 may be configured to yield in response to a force applied along a longitudinal axis of plunger 200. Once frangible region 206 yields (i.e., upon injection), a region 208 of proximal portion 202 adjacent frangible region 206 may be adapted to rotate away from a region 210 of distal portion 204 adjacent frangible region 206.

One or more surfaces 212 of proximal portion 202 that are proximal to frangible region 206 may be planar and may be at an angle relative to the longitudinal axis of plunger 200. Accordingly, as shown in FIG. 16, each surface 212 of proximal portion 202 may guide region 210 of distal portion 204 away from region 208 of proximal portion 202 after proximal portion 202 and distal portion 204 have uncoupled. This may prevent region 208 of proximal portion 202 from catching on region 210 as distal portion 204 is withdrawn, so that proximal portion 202 may remain lodged in the injectate chamber. The guidance provided by surface 212 on region 210 of distal portion 204 may, in some embodiments, cause one or more of proximal portion 202 and distal portion 204 to rotate about the longitudinal axis of plunger 200 relative to one another, as shown by the arrows in FIG. 16.

Similarly, one or more surfaces 214 of distal portion 204 that are distal to frangible region 206 may be planar and may be at an angle relative to the longitudinal axis of plunger 200. Accordingly, each surface 214 of distal portion 204 may guide region 208 of proximal portion 202 away from region 210 of distal portion 204 after distal portion 204 and proximal portion 202 have uncoupled. The guidance provided by surface 214 on region 208 of proximal portion 202 may, in some embodiments, cause one or more of proximal portion 202 and distal portion 204 to rotate about the longitudinal axis of plunger 200 relative to one another, as shown by the arrows in FIG. 16.

Although the present invention has been shown and described with reference to the foregoing operational principles and preferred embodiments, it will be apparent to those skilled in the art that various changes in form and detail can be made without departing from the spirit and scope of the invention. The present invention is intended to embrace all such alternatives, modifications and variances. The subject matter of the present invention includes all novel and non-obvious combinations and subcombinations of the various elements, features, functions and/or properties disclosed herein. Inventions embodied in various combinations and subcombinations of features, functions, elements, and/or properties may be claimed through presentation of claims in a subsequent application.

What is claimed is:

1. A nozzle assembly for a needle-free injection device comprising:
    a nozzle body including an injectate chamber and an outlet orifice; and
    a plunger configured to move through the injectate chamber toward the outlet orifice, the plunger including a proximal portion, a distal portion and frangible region along which the proximal portion and distal portion are configured to uncouple upon injection;
    wherein the proximal portion is adapted to rotate relative to and away from the distal portion about a longitudinal axis of the plunger upon injection, the rotation being sufficient to prevent the proximal region from catching on the distal portion when the distal portion is withdrawn;
    wherein the proximal portion remains in the injectate chamber upon retraction of the distal portion from the injectate chamber.

2. The nozzle assembly of claim 1, wherein the proximal portion is configured to lodge in a proximal end of the injectate chamber, thereby preventing intake of an injectate into the injectate chamber.

3. The nozzle assembly of claim 1, wherein the frangible region is configured to yield in response to a force applied along a longitudinal axis of the plunger.

4. The nozzle assembly of claim 3, wherein a surface of the proximal portion that is proximal to the frangible region is planar and is at an angle relative to the longitudinal axis.

5. The nozzle assembly of claim 4, wherein the surface of the proximal portion guides the region of the distal portion adjacent the frangible region away from the region of the proximal portion adjacent the frangible region after the proximal portion and the distal portion have uncoupled.

6. The nozzle assembly of claim 3, wherein a surface of the distal portion that is distal to the frangible region is planar and is at an angle relative to the longitudinal axis.

7. The nozzle assembly of claim 6, wherein the surface of the distal portion guides the region of the proximal portion adjacent the frangible region away from the region of the distal portion adjacent the frangible portion after the proximal portion and the distal portion have uncoupled.

8. The nozzle assembly of claim 3, wherein the region of the proximal portion adjacent the frangible region is adapted to rotate away from the region of the distal portion adjacent the frangible region about the longitudinal axis of the plunger.

9. A plunger for use in a needle-free injection device comprising:
    a plunger configured to move through an injectate chamber of the needle-free device toward an outlet orifice, the plunger including a proximal portion, a distal portion and a frangible region along which the proximal portion and distal portion are configured to uncouple upon injection;
    wherein the proximal portion is adapted to rotate relative to and away from the distal portion about a longitudinal axis of the plunger upon injection, the rotation being sufficient to prevent the proximal region from catching on the distal portion when the distal portion is withdrawn; and
    wherein the proximal portion remains in the injectate chamber upon retraction of the distal portion from the injectate chamber.

10. The plunger of claim 9, wherein the proximal portion is configured to lodge in a proximal end of the injectate chamber, thereby preventing intake of an injectate into the injectate chamber.

11. The plunger of claim 9, wherein the frangible region is configured to yield in response to a force applied along a longitudinal axis of the plunger.

12. The plunger of claim 11, wherein a surface of the proximal portion that is proximal to the frangible region is planar and is at an angle relative to the longitudinal axis.

13. The plunger of claim 12, wherein the surface of the proximal portion guides the region of the distal portion adjacent the frangible region away from the region of the proximal portion adjacent the frangible region after the proximal portion and the distal portion have uncoupled.

14. The plunger of claim 11, wherein a surface of the distal portion that is distal to the frangible region is planar and is at an angle relative to the longitudinal axis.

15. The plunger of claim 14, wherein the surface of the distal portion guides the region of the proximal portion adjacent the frangible region away from the region of the distal portion adjacent the frangible portion after the proximal portion and the distal portion have uncoupled.

16. The plunger of claim 11, wherein the region of the proximal portion adjacent the frangible region is adapted to rotate away from the region of the distal portion adjacent the frangible region about the longitudinal axis of the plunger.

17. A nozzle assembly for an injection device comprising:
a nozzle body including an injectate chamber and an outlet orifice; and
a plunger configured to move through the injectate chamber toward the outlet orifice, the plunger including a proximal portion, a distal portion, a frangible region along which the proximal portion and distal portion are configured to uncouple upon injection, a first surface proximal to the frangible region that is at an angle relative to a longitudinal axis of the injection device, and a second surface distal to the frangible region that is at an angle relative to the longitudinal axis of the injection device;
wherein the first surface guides the proximal portion to rotate about a longitudinal axis of the plunger relative to and away from the distal portion during injection, the rotation being sufficient to prevent the proximal region from catching on the distal portion when the distal portion is withdrawn;
wherein the second surface guides a region of the proximal portion adjacent the frangible region away from a region of the proximal portion adjacent the frangible region during injection; and
wherein the proximal portion remains in the injectate chamber upon retraction of the distal portion from the injectate chamber.

* * * * *